United States Patent
Baigar et al.

(10) Patent No.: US 9,956,651 B2
(45) Date of Patent: May 1, 2018

(54) METHOD FOR PRODUCING A FLUIDIC CONNECTION COMPONENT FOR CHROMATOGRAPHY

(71) Applicant: DIONEX SOFTRON GMBH, Germering (DE)

(72) Inventors: Erik Baigar, Munich (DE); Christian Andreas Hilmer, Germering (DE); Andreas Unger, Garching (DE)

(73) Assignee: Dionex Softron GmbH, Germering (DE)

( * ) Notice: Subject to any disclaimer, the term of this patent is extended or adjusted under 35 U.S.C. 154(b) by 468 days.

(21) Appl. No.: 14/200,392

(22) Filed: Mar. 7, 2014

(65) Prior Publication Data
US 2014/0259616 A1   Sep. 18, 2014

(30) Foreign Application Priority Data
Mar. 12, 2013   (DE) .......... 10 2013 102 439

(51) Int. Cl.
*B23P 19/04*  (2006.01)
*B23P 11/02*  (2006.01)
(Continued)

(52) U.S. Cl.
CPC ........ *B23P 11/025* (2013.01); *G01N 30/6026* (2013.01); *B01L 3/563* (2013.01);
(Continued)

(58) Field of Classification Search
CPC ... B23B 31/02; B23B 31/117; B23B 31/1179; B23B 2240/28; B23P 11/00;
(Continued)

(56) References Cited

U.S. PATENT DOCUMENTS 3,332,316 A    7/1967  Saunders
3,547,162 A *  12/1970 Schaerer ................. F16L 9/133
                                                 138/124
(Continued)

FOREIGN PATENT DOCUMENTS

CN    201000423 Y    1/2008
CN    201464357 U    5/2010
(Continued)

OTHER PUBLICATIONS

Barka et al., "Wege zur Miniaturisierung von Analysensystemen," Tiel 3: Automatische probeninjektion, LaborPraxis, Nov. 1997.
(Continued)

*Primary Examiner* — Sarang Afzali
*Assistant Examiner* — Darrell C Ford (57) ABSTRACT

A method for producing a fluidic connection component for chromatography is described. A connection component includes a main body and at least one insert held in the main body. The main body is prefabricated with an aperture for the at least one insert. The at least one insert is connected to the main body securely and fluidically tightly by a thermal process and by making use of a thermal expansion of the main body and/or of the insert that occurs during the thermal process. The method may include a thermally induced change in volume of the main body and/or of the insert that is retained after completion of the thermal process. The material and the geometry of the main body and of the insert and the thermal process are chosen such that, after completion of the thermal treatment, there is a secure and fluidically tight connection.

19 Claims, 2 Drawing Sheets

(51) Int. Cl.
  *B21D 39/00* (2006.01)
  *G01N 30/60* (2006.01)
  *B01L 3/00* (2006.01)

(52) U.S. Cl.
  CPC ...... *Y10T 29/4987* (2015.01); *Y10T 29/49863* (2015.01); *Y10T 29/49865* (2015.01); *Y10T 29/53704* (2015.01)

(58) Field of Classification Search
  CPC ....... B23P 11/005; B23P 11/02; B23P 11/022; B23P 11/025; B23P 11/027; B23P 2700/11; Y10T 29/53704; Y10T 29/49863; Y10T 29/49865; Y10T 29/4987; B21D 39/031; B21D 39/04; B21D 39/046; B21D 39/048; B21D 39/042
  USPC ......... 29/243, 446, 447, 450, 505, 506, 507, 29/508, 523
  See application file for complete search history.

(56) References Cited

U.S. PATENT DOCUMENTS

| | | | |
|---|---|---|---|
| 3,552,864 A | 1/1971 | Shields | |
| 4,076,420 A | 2/1978 | De Maeyer et al. | |
| 4,152,818 A * | 5/1979 | Mort | B21D 39/06 285/382.2 |
| 4,178,057 A | 12/1979 | McCormick | |
| 4,178,067 A | 12/1979 | Johnson et al. | |
| 4,198,081 A * | 4/1980 | Harrison | F16L 13/004 148/402 |
| 4,575,424 A | 3/1986 | Allington et al. | |
| 4,580,901 A | 4/1986 | Goldsmith | |
| 4,588,893 A | 5/1986 | Vidrine et al. | |
| 4,649,492 A * | 3/1987 | Sinha | B21D 39/203 29/421.1 |
| 4,747,687 A | 5/1988 | Hoppe et al. | |
| 4,886,356 A | 12/1989 | Paradis | |
| 5,003,174 A | 3/1991 | Datwyler et al. | |
| 5,097,211 A | 3/1992 | Schonstedt | |
| 5,124,130 A | 6/1992 | Costello et al. | |
| 5,131,583 A * | 7/1992 | Matsumoto | B21C 37/06 228/127 |
| 5,139,333 A | 8/1992 | Reinhard | |
| 5,140,169 A | 8/1992 | Evens et al. | |
| 5,217,808 A * | 6/1993 | Cobb | G02B 6/443 174/23 C |
| 5,240,537 A | 8/1993 | Bodicky | |
| 5,259,112 A * | 11/1993 | Matte | B29D 23/003 29/447 |
| 5,417,925 A | 5/1995 | Goodale et al. | |
| 5,422,971 A | 6/1995 | Honjo et al. | |
| 5,650,846 A | 7/1997 | Yin et al. | |
| 5,692,088 A * | 11/1997 | Ishiharada | B29C 47/0014 385/123 |
| 5,814,742 A | 9/1998 | Vissers et al. | |
| 5,905,271 A | 5/1999 | Wynn | |
| 6,122,049 A | 9/2000 | Sugiyama et al. | |
| 6,188,813 B1 | 2/2001 | Dourdeville et al. | |
| 6,200,531 B1 | 3/2001 | Liljestrand et al. | |
| 6,300,082 B1 * | 10/2001 | Erb | G01N 21/648 385/12 |
| 6,315,958 B1 | 11/2001 | Singh-Gasson et al. | |
| 6,444,175 B1 | 9/2002 | Singh-Gasson et al. | |
| 6,484,569 B1 | 11/2002 | Plant et al. | |
| 6,526,188 B2 | 2/2003 | Dourdeville et al. | |
| 6,587,195 B1 * | 7/2003 | Jennings | G01N 21/03 250/343 |
| 6,747,740 B1 | 6/2004 | Leveille et al. | |
| 6,867,857 B2 | 3/2005 | Hobbs | |
| 7,184,141 B2 | 2/2007 | Brewer et al. | |
| 7,948,621 B2 | 5/2011 | Burns et al. | |
| 9,581,468 B2 * | 2/2017 | Nguyen | B23P 11/005 |
| 9,585,781 B2 * | 3/2017 | Fischell | A61F 2/958 |
| 2002/0038998 A1 | 4/2002 | Fujita et al. | |
| 2003/0118485 A1 | 6/2003 | Singh-Gasson et al. | |
| 2004/0027568 A1 | 2/2004 | Maiefski et al. | |
| 2004/0036987 A1 | 2/2004 | Wisecarver et al. | |
| 2004/0066509 A1 | 4/2004 | Canty et al. | |
| 2004/0080744 A1 | 4/2004 | Hobbs | |
| 2005/0104607 A1 | 5/2005 | Byington et al. | |
| 2005/0213088 A1 | 9/2005 | Brewer et al. | |
| 2007/0041009 A1 | 2/2007 | Iwano et al. | |
| 2007/0064226 A1 | 3/2007 | Kolp et al. | |
| 2007/0077546 A1 | 4/2007 | Ji et al. | |
| 2008/0113447 A1 | 5/2008 | Krager et al. | |
| 2008/0231042 A1 * | 9/2008 | Brayman | B23P 11/025 285/41 |
| 2008/0236720 A1 * | 10/2008 | Sigler | B29C 37/0085 156/73.5 |
| 2009/0033022 A1 * | 2/2009 | Iki | B65H 27/00 271/109 |
| 2009/0321356 A1 * | 12/2009 | Gerhardt | G01N 30/6095 210/656 |
| 2010/0037706 A1 | 2/2010 | Sparks et al. | |
| 2010/0118298 A1 | 5/2010 | Bair et al. | |
| 2011/0064354 A1 * | 3/2011 | Nishio | G02B 6/4214 385/14 |
| 2011/0180211 A1 | 7/2011 | Jurischka et al. | |
| 2011/0194887 A1 * | 8/2011 | Mankame | F16B 1/0014 403/28 |
| 2011/0299067 A1 * | 12/2011 | Yokoyama | G01N 21/05 356/213 |
| 2013/0242296 A1 | 9/2013 | Kenyon | |
| 2014/0266266 A1 | 9/2014 | Baigar et al. | |
| 2016/0327194 A1 * | 11/2016 | Wells | F16L 25/01 |
| 2017/0016541 A1 * | 1/2017 | Pears | F16K 1/30 |
| 2017/0239733 A1 * | 8/2017 | Fronius | B23B 31/1179 |

FOREIGN PATENT DOCUMENTS

| | | |
|---|---|---|
| CN | 201765178 U | 3/2011 |
| DE | 3603905 A1 | 8/1986 |
| DE | 3605518 A1 | 8/1987 |
| DE | 102007048738 | 4/2009 |
| DE | 102008027026 A1 | 12/2009 |
| EP | 0847767 B1 | 2/2005 |
| EP | 0956634 B1 | 10/2005 |
| JP | 4873193 | 10/1973 |
| JP | 59180448 | 10/1984 |
| JP | 60148956 | 10/1985 |
| JP | 02042337 | 2/1990 |
| JP | 02134563 | 5/1990 |
| JP | 05187995 | 7/1993 |
| JP | 8500188 | 1/1996 |
| JP | 9178648 | 7/1997 |
| JP | 2007047176 | 2/2007 |
| JP | 2011007758 | 1/2011 |
| WO | 2005015162 A2 | 2/2005 |
| WO | 2007009493 A1 | 1/2007 |
| WO | 2011079058 A1 | 6/2011 |
| WO | 2013113402 A1 | 8/2013 |

OTHER PUBLICATIONS

Dionex Corporation, PDA-100 (USB) Photodiode Array Detector Operator's Manual, Revision 03, Mar. 2006, 132 pages.
Dionex Corporation, UVD 170U and UVD 340U UV/VIS Detectors Operating Instructions, Revision 1.0-a, Jul. 2003, 54 pages.
Van Der Vlis, "Development of a needle device for on-line electroextraction-liquid chromatography," J. Chromatogr. A, 741, 13-21, 1996.
Vissers et al., "A fully automated microautosampler for micro and capillary liquid chromatography," International Laboratory, Jan. 1996.

* cited by examiner

Fig. 2

METHOD FOR PRODUCING A FLUIDIC CONNECTION COMPONENT FOR CHROMATOGRAPHY

CROSS REFERENCE TO RELATED APPLICATIONS

This application is claims the priority benefit under 35 U.S.C. § 119 to German Patent Application No. 10 2013 102 439.4, filed on Mar. 12, 2013, entitled "Method for producing a connection component, in particular a fluidic connection component for chromatography" the disclosure of which is incorporated herein by reference.

FIELD OF THE INVENTION

The invention concerns a method for producing a connection component, in particular a fluidic connection component for chromatography, which consists of a main body and at least one insert held securely and/or fluidically tightly in the main body.

BACKGROUND

In chromatographic applications, for example in liquid chromatography, it is necessary for a wide variety of purposes to couple liquid-carrying capillaries or else optical waveguides to chromatographic components, such as chromatography columns or sensors. Connection devices or connection components of various embodiments are used for this. The connection components, in particular socket or plug devices, may also be releasably or unreleasably connected to the chromatography component concerned and form a constituent part of the component.

In all of these applications it is necessary to connect the connection component or the fluid capillary that is releasably or unreleasably connected to the connection component, or the optical waveguide connected thereto, fluid-tightly to the respective chromatography component. The fluid capillary to be connected or the optical waveguide to be connected or any other component that is to be respectively connected fluid-tightly to a chromatography component is referred to hereinafter as the insert, which is coupled to the chromatography component by means of a connection component (which may also consist of multiple individual parts).

In this respect, WO 2011/079058 A1 discloses for example a fluidic connection device in which an optical waveguide in the form of an optical fiber is fixed by means of clamping parts in a main body that has an axial bore in such a way that it passes through the axial bore. In the front region, the aperture in the main body is of a conically tapering form. A plastically deformable plastic part with a central bore through which the optical fiber to be fixed protrudes is inserted into this conical taper. The plastic part is likewise formed in a complementarily conical form in its front region and is axially acted upon on its rear side by a further hollow-cylindrical clamping part. This further hollow-cylindrical clamping part is connected to the main body in the form of an interference fit during an axial pressing-in process and acts upon the front conical clamping part. In the pressing-in process, the front conical clamping part is axially acted upon by the hollow-cylindrical clamping part and pressed into the conical region of the main body with such a great force that a fluidically tight connection and simultaneous fixing of the optical fiber in the main body are obtained. In the final state, the optical fiber may finish flush with the end face of the main body or protrude from it, possibly together with an un-formed front region of the conical clamping part.

Disadvantages of this are the use of multiple clamping parts and the use of an interference fit for the hollow-cylindrical clamping part, with the result that it is only with difficulty that a defined axial force can be applied to the front, conical clamping part for pressing it into the conical region of the main body.

Furthermore, WO 2007/009493 A1 discloses a coupling device in which a chromatography component, such as a chromatography column, already has a socket-like unit, into which a fluid-carrying capillary can be inserted. The socket unit has a projecting cylindrical region, onto which a hollow-cylindrical part can be mounted, the hollow-cylindrical part also encompassing with its rearward region the end face of the hollow-cylindrical region of the socket. After being mounted onto the hollow-cylindrical region of the socket, the hollow-cylindrical part, which consists of a thermoplastic material, is shaped by means of a mold in such a way that a radially inwardly directed pressure is obtained and, moreover, the rearward region of the hollow-cylindrical, shaped part finishes flush with the outer circumference of the inserted capillary and becomes connected to it. The plastic shaping process consequently produces a fluid-tight connection. At the same time, during the cooling of the shaped hollow-cylindrical connection part there is the additional effect that, as a result of the greater coefficient of thermal expansion of this thermoplastic material in comparison with the material of the fluid-carrying capillary, an even greater radially inwardly directed pressure, and consequently corresponding holding forces, are exerted on the capillary.

A disadvantage of this, however, is that such a connection of a capillary to a chromatography component no longer allows the capillary to be released. Moreover, the thermal shaping of the hollow-cylindrical connection part under pressure requires a corresponding amount of effort. In addition, the melting of at least partial regions of the prefabricated component may cause problems with the dimensional stability of the finished component produced, since the prefabricated part may be deformed by the melting process.

SUMMARY

Therefore, proceeding from this prior art, the invention is based on the object of providing a method for producing a connection component, in particular a fluidic connection component for chromatography, which can be carried out easily and with little effort and which ensures in an easy way a secure and/or fluidically tight connection between an insert and a main body of the connection component.

The invention is based on the recognition that a secure and/or fluidically tight connection between the main body and the at least one insert inserted into a corresponding aperture in the main body can be produced in an easy way by means of a purely thermal process. This involves using either the thermal expansion of the main body and/or of the insert that occurs during the thermal process or a thermally induced change in volume of the main body and/or of the insert that is retained after completion of the thermal process. A melting of partial regions of the main body or of the insert, in the sense of complete initial melting of at least the surface of the part concerned, which would lead to scarcely controllable deformation, is avoided. To create a secure and/or fluidically tight connection between the prefabricated main body and the at least one insert inserted into a corresponding aperture of the main body, either the main body or the insert or both parts is/are subjected to a thermal process, the at least one insert being inserted into the aperture provided for it in the main body and positioned before or during the implementation of the temperature profile—depending on the particular form of the method. The temperature profile should be chosen in this case in such a way that there is no initial or full melting of the contact regions (into a pasty or even liquid state of the material) between the main body and the insert, since this would mean that the exact position of the insert in the main body would no longer be ensured.

The method according to the invention consequently offers the advantage that it is not necessary to use in the front region of the insert that can come into contact with a fluid an adhesive or other additional material that is not inert with respect to the fluid in order to achieve a secure and/or fluidically tight connection between the insert and the main body. Furthermore, the method according to the invention avoids heating of the material of the main body into a temperature range in which the main body softens and is only brought into a form in which the main body encloses the insert in a secure or fluidically tight manner by the exertion of a pressure, for example by means of a shaping tool. In particular, initial melting of the material of the main body is also avoided, in order to bring about an intensive connection between the main body and the insert.

According to the invention, the insert must merely be prefabricated in such a way that the insert can be inserted into the aperture of the main body provided for it before or during the thermal process. The at least one insert is connected to the insert securely and/or fluidically tightly by the purely thermal process and by making use of a thermal expansion of the main body and/or of the insert that only occurs during the thermal process and/or by making use of a thermally induced change in volume of the main body and/or of the insert that is retained after completion of the thermal process. For this purpose, the material and the geometry of the main body and of the insert and the thermal process are chosen such that, after completion of the thermal treatment, such great radial clamping forces between the main body and the insert occur in a clamping region along the course of the aperture that there is a secure and/or fluidically tight connection between the main body and the insert at temperatures within a working temperature range.

A secure connection should be understood here as meaning a connection that is sufficiently secure to avoid the connection being released by such forces that act on the insert or the main body in the given application. The secureness of the connection (within the working temperature range) with respect to forces acting axially on the insert does not necessarily have to be so great that the insert cannot be pulled out of the main body or moved axially with respect to it without being destroyed. There just has to be sufficient axial secureness for the actual application. In many cases, however, depending on the materials and the thermal process, suitable dimensioning of the insert and the main body will make the connection only destructively releasable within the working temperature range.

Within the scope of the present description, fluidically tight means that a passing through of liquid (in particular under high pressure) into an intermediate space between the outer circumference or the outer walling of the insert and the inner walling of the aperture in the main body is avoided.

According to one particular form of the invention, the prefabricated main body and the insert may be formed in such a way that, after the thermal process, the at least one insert is connected fluidically tightly to the main body in the clamping region. The axial length of the clamping region should preferably be chosen such that the desired tightness and the desired holding forces for the fixing of the insert in the main body are achieved.

It goes without saying that, with regard to its dimensions and taking into consideration the thermal behavior of the material, the aperture in the main body must be made to match the geometry (and possibly the thermal behavior) of the insert, with the result that, after completion of the thermal process, the material of the main body is in contact over the entire circumferential walling of the insert within a predetermined (axial) clamping region and corresponding radial pressing forces are exerted to achieve the desired fluidically tight connection between the two parts. It goes without saying that a sufficient surface quality of the parts to be connected within the clamping region is a precondition for this.

According to one particular form of the invention, preferably a material with a higher coefficient of thermal expansion, in particular a plastic, may be used as the material for the main body and a material with a lower coefficient of thermal expansion, in particular glass, ceramic or metals and alloys thereof, may be used as the material for the insert. The coefficient of thermal expansion of the material of the main body is in this case preferably chosen to be at least twice the coefficient of thermal expansion of the material of the insert. This choice of materials is suitable in particular whenever the thermal process is devised in such a way that substantially only the main body is heated and the thermal expansion of the material is also, or predominantly, used for producing the radial clamping forces.

According to another alternative, a material with a higher coefficient of thermal expansion, in particular a plastic, may be used as the material for the at least one insert and a material with a lower coefficient of thermal expansion, in particular glass, ceramic or metal or a metal alloy, may be used as the material for the main body, the coefficient of thermal expansion of the material of the insert preferably being at least twice the coefficient of thermal expansion of the material of the main body. This choice of materials is suitable in particular whenever the thermal process is devised in such a way that substantially only the insert is cooled and the thermal expansion or contraction of the material as a result of cooling is also, or predominantly, used for producing the radial clamping forces.

Although the use of identical materials for the insert and the main body is also possible in principle, for the insertion of the insert into the aperture there must then be a sufficient temperature difference, and the insertion must take place so quickly that the final position of the insert within the aperture is reached before the insert heats up as a result of the contact with the material of the main body in such a way that the thermal expansion of the insert has the effect that the insert can no longer be positioned.

According to one particular form of the invention, for this purpose the main body is prefabricated in such a way that, within a working temperature range, the inner dimensions of the aperture are slightly smaller than the dimensions of the cross section of the insert (at least within the clamping region). The materials of the main body and of the insert may then be brought by means of the thermal process to a predetermined common temperature, which lies outside the working temperature range, or a predetermined temperature difference between the material of the main body and the material of the insert may be produced, the predetermined common temperature or the temperature difference being chosen with respect to the thermal expansion properties of the material of the main body and of the material of the at least one insert in such a way that the insert can be inserted into the aperture. It goes without saying that the insertion may also take place in the state in which there is a slight interference fit between the main body and the insert. Subsequently, the insert can be inserted into the aperture. The part of the thermal process following thereafter is devised in such a way that the insert is held securely and/or fluidically tightly in the main body at a temperature of the insert and the main body within the working temperature range. This part of the thermal process which then follows may consist in a simple cooling phase, unless further effects, such as a conditioning of one or both materials, is to take place.

The dimensions of the aperture of the prefabricated main body in comparison with the dimensions of the insert—with given materials—determine the pressing and holding forces between the main body and the insert (at least in the clamping region), unless there are also further effects, in particular the permanent increase or decrease in volume described below of one or both materials as a result of a transformation of material properties. The geometry required for this, with which the aperture in the main body must be prefabricated, can be easily ascertained by tests and/or by simulation.

A material which consists partially of a crystalline phase and partially of an amorphous phase, for example a thermoplastic, may be used as the material for the main body and/or as the material for the at least one insert. If such a material is chosen for both components, it may be the same material with the same or a different composition of the crystalline phase and the amorphous phase, or else different materials that both display corresponding properties. Thermoplastics with this property are, for example, materials from the group of polyether ketones, such as PEEK, PEKEK etc. These materials are mainly amorphous, but have a certain fraction of a crystalline phase. In the case of PEEK, with very slow cooling or after conditioning (i.e. keeping a temperature within a conditioning range for a predetermined time period), at most about 38% of the material is observed as a crystalline phase. Since the crystalline phase has a higher density in comparison with the amorphous phase, an increase in volume of the material is produced if the main body or the insert is heated beyond a melting temperature (for the crystalline phase) and subsequently cooled again relatively quickly, with the result that the fractions of the crystalline phase that are transformed into the amorphous phase by the melting solidify in their amorphous structure. After such a thermal treatment, the main body and the insert have a greater volume. The degree of the increase in volume depends in this case on the way in which the process is conducted.

This effect, referred to hereafter as swelling, can be reversed within certain limits by a conditioning process in which the main body or the insert is kept at a temperature within a conditioning range for a certain time. The conditioning range in this case lies below the melting temperature for the crystalline phase.

This swelling process, which may occur during the thermal process with a main body of a corresponding material and would initially lead to an undesired increase in volume (which would be accompanied by a reduction in the clamping forces), can be kept within limits by suitably controlling the process. In particular, the maximum temperature should in this case be chosen such that the melting temperature of the crystalline phase is either not exceeded, or is only exceeded for such a short time period that there is no conversion of the crystalline phase into the amorphous phase, or only to an admissible degree.

It goes without saying that the behavior of the material can also be determined by the choice of a specific initial state of the material. For example, a material with a very small crystalline fraction may be used. This can then also be heated to a higher temperature or heated to a higher temperature for longer, without any appreciable swelling process occurring.

According to another particular form of the invention, such swelling behavior may, however, also be deliberately used for increasing the holding forces between the main body and the insert, and consequently for producing better tightness. If greater pressing forces are not desired, the swelling behavior may also be used for choosing greater dimensions of the aperture in the phase in which the insert has to be inserted into the aperture. As a result, the insertion is made easier, for example over a greater axial length. The fraction of the crystalline phase in the material of the prefabricated main body and the temperature profile of the expansion and shrinkage process may therefore be chosen such that, after completion of the assembly method, a secure and fluid-tight fixing of the at least one insert in the main body with predetermined pressing or holding forces is obtained.

If the insert is produced from such a material displaying a swelling behavior and this material has a relatively great fraction of the crystalline phase, this fact can likewise be used to produce an increase in the clamping forces, in that, after the insertion of the insert into the aperture of the main body, an increase in volume is deliberately brought about by heating beyond the melting temperature of the crystalline phase. If swelling is to be avoided during the insertion, it is possible, in order to allow insertion into an undersized prefabricated aperture in the main body, that the main body is initially heated only to such a temperature that lies sufficiently below the melting temperature of the crystalline phase and, in addition or instead of this, sufficient cooling of the insert takes place. Subsequently, an increase in the clamping forces may then take place by increasing the temperature of the insert beyond the melting temperature of the crystalline phase and relatively rapid cooling. This produces swelling, and the change in volume concerned is retained even after the cooling.

In a further particular form of the invention, this swelling behavior of a partially crystalline material for the main body and/or the insert also allows the main body to be prefabricated in such a way that, within the working temperature range, the inner dimensions of the aperture in the initial state of the materials are slightly greater than the dimensions of the cross section of the insert. In this case, the insert can be inserted into the aperture of the prefabricated main body already in the cold state of the main body (that is to say at a temperature within the working range). Subsequently, a thermal process then has to be carried out in such a way that, after its completion (as a result of the chosen temperature profile of the process), the material characteristics of the material of the main body and/or of the insert have changed in such a way that sufficiently great clamping forces are produced as a result of the change(s) in volume.

If the main body is produced from such a material, the clamping forces can be produced by increasing the fraction of the crystalline phase, and the accompanying reduction in volume. It goes without saying that a material with a sufficiently great fraction of the amorphous phase must then be chosen as the starting material.

For this purpose, the main body must therefore be heated to a temperature within the conditioning range, in order to allow the conversion of the amorphous phase into a crystalline phase. The setting of the dimensions of the aperture in comparison with the dimensions of the cross section of the insert may in turn be determined by tests or by simulation. Moreover, here there is the possibility of continuing the conditioning process until the desired pressing or holding forces between the main body and the insert are achieved. The temperature and time required for this (that is to say the temperature profile suitable for this) can likewise be ascertained by tests or simulation.

If the insert is produced from such a material, the clamping forces can be produced by reducing the fraction of the crystalline phase and the accompanying increase in volume. It goes without saying that a material with a sufficiently great fraction of the crystalline phase must then be chosen as the starting material.

In this case, the main body will preferably be heated to a temperature above the melting temperature for the crystalline phase of the material of the insert, in order to bring about the conversion of the crystalline phase into an amorphous phase. The material of the main body may then either be a material that does not display such a swelling behavior or the melting temperature for the crystalline phase of the material of the main body lies much higher than the melting temperature for the crystalline phase of the material of the insert. The setting of the dimensions of the aperture in comparison with the dimensions of the cross section of the insert may in turn be determined by tests or by simulation. Moreover, here there is the possibility of continuing the conditioning process until the desired pressing or holding forces between the main body and the insert are achieved. The temperature and time required for this (that is to say the temperature profile suitable for this) can likewise be ascertained by tests or simulation.

It should once again be pointed out at this stage that, at the time of the insertion of the insert into the aperture of the main body, the dimensions of the aperture may be designed such that the insertion of the insert can take place without great force or else, because corresponding frictional forces act between the inner walling of the aperture in the main body and the circumference of the insert, i.e. there is already a slight interference fit, the insertion of the insert must already take place by means of a corresponding axial force. Said interference fit allows greater holding forces after completion of the thermal process, with the same dimensional changes of the main body or of the insert that are produced by thermal or material-induced shrinkage (transformation from the crystalline phase to the amorphous phase).

According to a further particular form of the invention, the expansion of the outer dimensions of the main body during the thermal process on at least one outer surface may be restricted by a molding element that is predetermined in its form or in its dimensions in such a way that a plastic deformation of the main body occurs in the region of the at least one outer surface.

This procedure may be used to produce reference surfaces on the outer surface with great accuracy, provide it with a suitable structure or simply improve the smoothness of the outer surface. For example, the circumferential surface of the main body may be produced with great accuracy in a partial region (this may be for example a cylindrical partial surface), not only with respect to a desired structure but also with respect to desired smoothness and/or desired dimensioning (in particular a specific outer diameter). Since the material contracts again during cooling, it goes without saying that this shrinkage must be taken into consideration in the dimensioning of the molding element.

An outer surface of the main body produced with such high precision can act for example as a guiding surface which interacts with a complementary element in order to achieve an exact positioning of the two components.

According to one particular form, the expansion of the outer dimensions of the main body may take place in a region radially surrounding the clamping region and an additional increase in the radial clamping forces may in this way be produced in the region of the clamping region by the plastic deformation, since the increase in volume is restricted outwardly in the radial direction, and accordingly the increase in volume enforces a plastic deformation of the material into the radially inner region concerned.

According to a further particular form of the invention, during the cooling or conditioning of the main body, the shrinkage process on at least one inner surface of the main body may be restricted by a molding element in such a way that a plastic deformation of the main body occurs in the region of the at least one inner surface. Here, therefore, an inner surface is produced with great accuracy by the main body encompassing the molding element and being shrunk onto it. To be able to release the main body again from the molding element after completion of the shrinkage process, it may be necessary to heat the main body again slightly, in order to reduce the holding forces. It goes without saying that the heating must in this case take place in such a way that, as far as possible, there is no renewed swelling of the material, that is to say transformation from the crystalline phase into an amorphous phase.

In the case of these variants of the method according to the invention, it goes without saying that it is necessary that the molding element has a lower coefficient of thermal expansion than the material of the main body.

According to the invention, the at least one insert, which may be an optical waveguide or a fluid capillary, may have a coating, which is removed in the front region, in which the insert is connected to the main body by the thermal expansion and shrinkage process. This always becomes necessary whenever the coating is not sufficiently thermally stable, durable in the long term or inert with respect to the fluids to be used. The removal of the coating must also always be considered whenever the coating has not been applied with sufficient precision with respect to the longitudinal axis of the insert, for example has an uneven thickness as seen over the circumference. This would lead to eccentric positioning of the insert with respect to the longitudinal axis of the aperture.

Since, however, the coating has the effect of protecting the circumferential surface of the insert, according to the invention a rearward region of the insert, in which the coating has been removed and which lies on the side of the clamping region that is facing away from the front end of the insert, may be protected, and preferably connected to the main body, with an adhesive material. For this purpose, the aperture may be increased in size in a rearward region (with respect to the clamping region) with regard to its cross-sectional dimensions, with the result that the adhesive material can be introduced in the annular region between the inner walling of the aperture and the outer walling of the insert. It is also possible to form the aperture here in such a way as to allow the introduction of a supporting element, which is likewise passed through by the insert and which can be connected by an adhesive material to the insert and the main body both on the inside (that is to say between the inner walling of the supporting element and the outer walling of the insert) and on the outside (that is to say between the outer walling of the supporting element and the inner walling of the aperture in the main body). Such a supporting element can improve the mechanical stability of the insert where it leaves the main body (the supporting element may protrude out of the aperture of the main body) and also act as a means of relieving tension and preventing buckling.

The method according to the invention is also suitable in particular for producing a connection component with two or more inserts, the main body being prefabricated with at least two apertures, and two or more inserts being connected to the main body securely and/or fluidically tightly by a single thermal process.

BRIEF DESCRIPTION OF THE DRAWINGS

The invention is explained in more detail below on the basis of exemplary embodiments that are represented in the drawing.

DETAILED DESCRIPTION OF EMBODIMENTS

The connection component 1 (hereinafter connection component 1 and optical plug 1 can be used interchangeably) that is represented in a schematic longitudinal section in FIG. 1 comprises a main body 3, which has an axial aperture 5, in which an optical waveguide 7 is held. The axial aperture 5 fixes the optical waveguide 7 in a clamping region 11, which is provided in the front region of the main body and has a predetermined axial extent. The axial extent of the clamping region 11 is in this case chosen such that, after the production method explained below, a sufficiently secure and possibly fluidically tight mounting of the optical waveguide 7 in the main body 3 is obtained. Provided in the end face 3a of the main body 3 is a recess 13, which serves for the coupling of the optical plug 1 to a further component, for example to an optical source. The inner walling 13a of the recess 13, running substantially parallel to the longitudinal axis of the optical plug, serves for the exact positioning of the plug with respect to the component be coupled. The diameter of the recess 13 must consequently be aligned with sufficient accuracy concentrically in relation to the longitudinal axis of the optical plug and in relation to the longitudinal axis of the optical waveguide 7.

In the rearward region of the main body 3, the aperture 5 is provided after the clamping region 11 with a cross section that is greater in comparison with the clamping region 11. This region 15 is intended for receiving an adhesive material. The adhesive material (not depicted) is introduced in the axial region 15 of the aperture 5 and completely fills the annular region concerned between the inner walling of the aperture 5 in the region 15 and the outer walling of the optical waveguide 7. Consequently, in this region, the adhesive material protects the circumferential surface of the optical waveguide 7, which in the entire front region of the optical waveguide is free from a protective coating 7a. The coating is removed in the front region in order to achieve positioning of the optical waveguide 7 in the main body 3 that is as precise as possible. This is so because such protective coatings, which may consist of a softer plastics material, usually have a relatively uneven thickness as seen axially or else over the circumferential direction. This could lead to insufficiently exact concentric fixing of the optical waveguide 7 by the clamping on a coating 7a in the clamping region 11.

The adhesive material may also serve the purpose of ensuring the axial secureness of the connection between the optical waveguide 7 and the main body 3 if the radial pressing forces in the clamping region 11 cannot ensure sufficient axial secureness even though they bring about the fluidic tightness of the connection.

Figure 1:
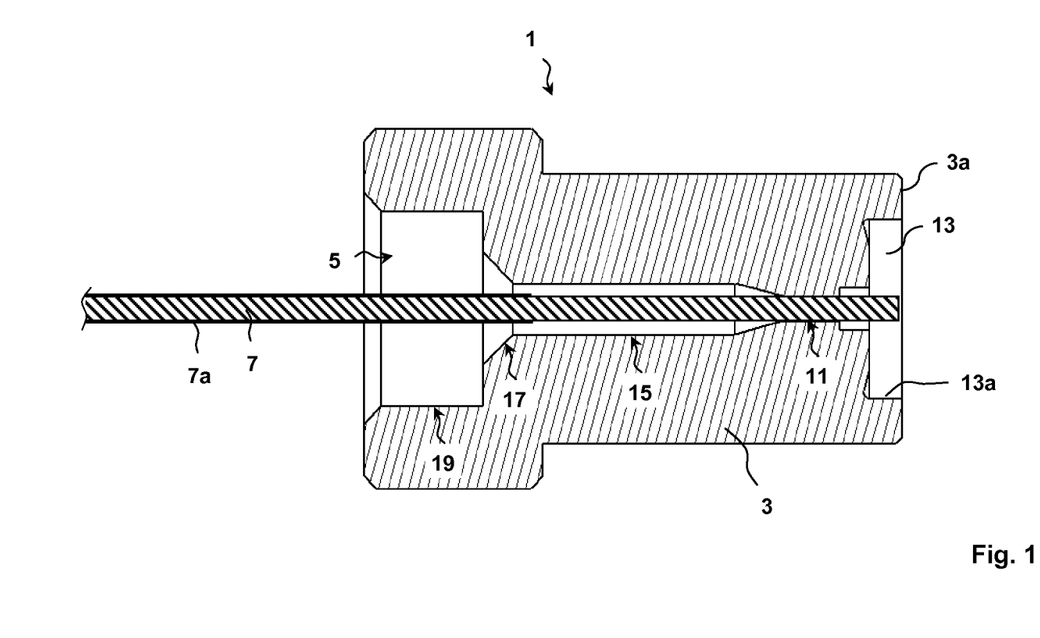
FIG. 1 shows a schematic longitudinal section through a connection component produced by the method according to the invention in the form of an optical waveguide plug, in which an optical waveguide is held securely in a main body.

The adhesive material, which is not represented in FIG. 1, fills the region 15, preferably into the conically widening region 17 of the aperture 5 that is provided after the region 15 in the direction of the end region of the main body 3. The region 19 that follows after the region 17 and has a further increased diameter or cross section may possibly also be entirely or partially filled with the adhesive material.

The connection component represented in FIG. 2 in the form of a coupling element 100 (hereinafter coupling element 100 and connection component 100 can be used interchangeably) likewise has a main body 103, in which in turn an optical waveguide 7 is held securely and fluidically tightly. The main body 103 has substantially the same form and the same dimensioning as the main body 3 of the optical plug in FIG. 1. Therefore, corresponding parts and regions of the main body 103 are denoted by identical reference signs as in the case of the main body 3 in FIG. 1. In addition, a fluid capillary 105, which is likewise coated with a coating 105a, is held in the main body 103 of the coupling element 100. The main body 103 has a further aperture 107, in which a supporting element 109 is also inserted and fixed along with the fluid capillary 105.

The aperture 107 is connected in the front region to the aperture 5 for the optical waveguide 7. For this purpose, the aperture 5 is slightly widened in the front region of the coupling element 100, that is to say in front of the clamping region 11, in comparison with the clamping region 11. The slightly widened region 111 opens out in turn into a recess 113, which has a greater diameter in comparison with the widened region 111 and is formed concentrically in relation to the longitudinal axis of the main body 103 and concentrically in relation to the longitudinal axis of the optical waveguide 7. The recess 113 serves for receiving an annular seal 115, which serves for the fluidic coupling of the coupling element 100 to a further component, for example to a measuring cell for a chromatographic device (not represented).

The annular seal 115 is formed in such a way that, even when coupling to the further component has taken place, it leaves an annular space between the outer walling of the optical waveguide 7 and the inner walling of the seal. The resultant annular space may for example be dimensioned in such a way that it approximately coincides with the annular space formed by the widened region 111. This has the advantage in chromatography that a low-dispersion connection is created.

The aperture 107 has in its front end a clamping region 117 for the fluid capillary 105, which in this region is free from the coating 105a, in order to allow the most concentric possible fixing and sufficient fixing in the clamping region 117. The angle between the longitudinal axis of the apertures 107 and 5 and between the longitudinal axis of the fluid capillary 105 and the optical waveguide 7 is chosen such that easy production and assembly is possible and, moreover, the fluid flow after leaving the fluid capillary 105 can enter as optimally as possible into the widened region 111 or the annular space formed as a result. In the rearward region, the aperture 107 is widened after the clamping region 117 over a conical region 119 into a region 121 with a further increased inner diameter. The hollow-cylindrical supporting element 109, which encompasses the fluid capillary 105, reaches into the region 121. After the fixing of the optical waveguide 7 and the fluid capillary 105 by the assembly method explained below, the annular space between the outer diameter of the fluid capillary 105 and the inner walling of the supporting element 109 as well as the conically widening region 119 may be filled with an adhesive material to achieve improved mechanical stability and tension relief for the fluid capillary 105. The supporting element 109 may likewise be adhesively cemented into the region 121. However, it is also possible to fix the supporting element 109 in the main body 103 by means of the expansion and shrinkage process explained below.

Figure 2:
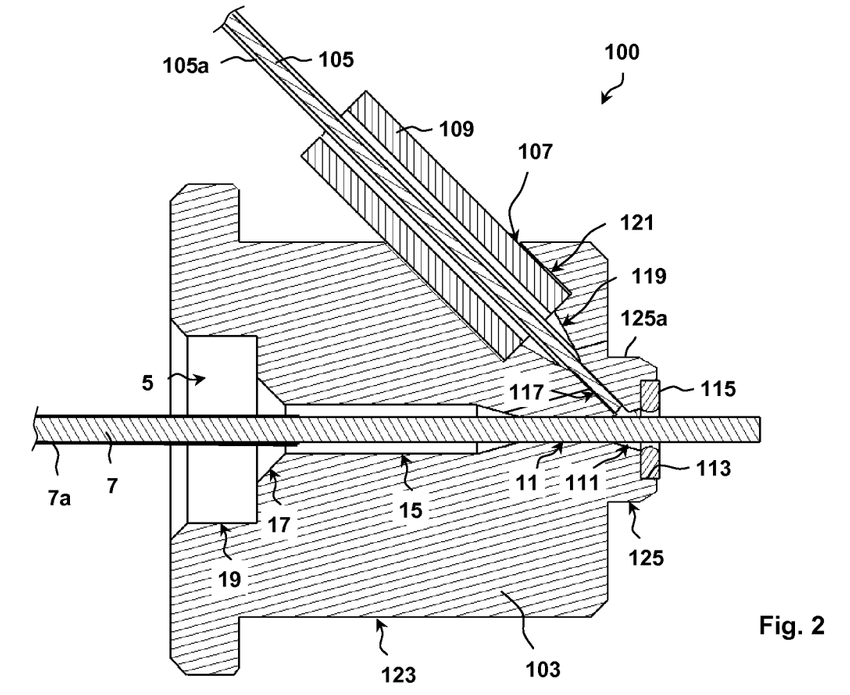
FIG. 2 shows a connection component produced by the method according to the invention in the form of a coupling element for a measuring cell for chromatographic applications, with a main body in which an optical waveguide and a fluid-carrying capillary are held securely and fluidically tightly.

In the case of the variant that is represented in FIG. 2, the main body has a substantially circular-cylindrical form in the middle region 123. The diameter of this region may serve the purpose of achieving during the assembly of the coupling element 100 with the component to be connected thereto a sufficient pre-guidance, which is enough to introduce the part of the optical waveguide 7 protruding beyond the end face of the coupling element into a corresponding recess of the further component without any damage to the optical waveguide taking place.

On its front side, the main body 103 has a positioning region 125, which has a reduced diameter in comparison with the middle region 123. This substantially cylindrical region serves for the exact positioning of the coupling element in the component receiving the coupling element 100. This receiving component has for this purpose a recess of a complementary form, the inner diameter of which corresponds substantially to the outer diameter of the positioning region 125. The positioning region 125 must consequently be produced very exactly coaxially in relation to the longitudinal axis of the main body 103 and in relation to the longitudinal axis of the optical waveguide 7 fixed in the main body.

The production of the optical plug 1 that is shown in FIG. 1 or of the coupling element 100 that is shown in FIG. 2 can be carried out according to the invention as follows:

The main body 3 or 103, consisting of a material with a greater coefficient of thermal expansion, is first prefabricated with sufficient accuracy. This also involves already producing the apertures 5 and 107.

The apertures 5, 107 in the clamping regions 11, 117 are prefabricated in such a way that these regions have slightly smaller cross-sectional dimensions than the cross-sectional dimensions of the respective insert that is to be fixed in the respective clamping region. In a thermal process, the cross-sectional dimensions of the main body 3, 103 in the clamping region 11, 117, 121 are widened in comparison with the cross-sectional dimensions of the insert in such a way that the insert 7, 105, 109 can be inserted into the aperture 5, 107 concerned and, after completion of the thermal process, sufficiently great radial clamping forces are obtained to connect the insert 7, 105, 109 securely and/or fluidically tightly to the main body at temperatures within a predetermined working temperature range for the connection component 1, 100 (i.e. at substantially the same temperature for the insert part and the main body or with a sufficiently small temperature difference within which the clamping forces are still sufficiently great).

The material of which the fluid capillary 105 and the optical waveguide 7 consist (glass, metal or metal alloys, such as for example steel or titanium and corresponding alloys, on the one hand, and glass or plastic on the other hand) has a lower coefficient of thermal expansion than the material of the main body. For the main body 3, 103, a material of which the coefficient of thermal expansion is at least twice the coefficient of thermal expansion of the material for the optical waveguide 7 and the fluid capillary 105 is preferably chosen.

Although the method could in principle also be carried out with materials for the optical waveguide 7 and the fluid capillary 105 and also the main body 3, 103 that have very similar or even identical coefficients of thermal expansion, this would make the production process more difficult. In particular, when the inserts, that is to say the optical waveguide 7, the fluid capillary 105 and possibly the supporting element 109, are inserted, there must be a sufficient temperature difference between these components and the main body, and the insertion must be carried out sufficiently quickly before the inserts assume a higher temperature and, as a result of the accompanying expansion, can no longer be inserted into the clamping regions, which are produced as only slightly larger (this applies at least whenever a thermal expansion of the main body is necessary for the insertion and the cross section of the clamping regions is not chosen to be greater at the initial temperature than the dimensions of the insert concerned).

In a next step, at least in the region of the clamping regions 11, 117, the main body may then be brought to a higher temperature, which is sufficient to widen the cross-sectional dimensions of the respective clamping region 11, 117 as a result of the thermal expansion of the material in such a way that the insert can be inserted into the aperture 5, 105 or the clamping region 11, 117 and axially positioned.

After cooling, the insert is then fixed in the clamping region 11, 117. It goes without saying that, for this purpose, the initial dimensions of the apertures in the clamping regions 11, 117 must be chosen with respect to the outer dimensions of the inserts in such a way that, after the cooling to a temperature within a working range, sufficient fixing and holding forces are obtained.

At least in the case of the coupling element 100 that is shown in FIG. 2, the holding forces and the geometry of the clamping region 11, 117 must also be chosen such that, after the cooling, fixing is obtained in such a way that the connection is also fluidically tight. This also presupposes a sufficient surface quality.

Furthermore, it goes without saying that it would also be possible in the case of materials with different coefficients of thermal expansion to heat both components in such a way that, at a target temperature, an aperture that is sufficiently large in comparison with the outer dimensions of the insert is obtained in the main body.

Finally, instead of just heating the main body, cooling of the insert may also or additionally take place, with the result that its outer dimensions (in cross section) are reduced.

In a further variant, a material with a greater coefficient of thermal expansion may be chosen for the insert, with the result that, just by cooling it (or possibly with additional heating of the main body), the insert can be inserted into the aperture concerned.

After the fixing of the insert elements in the clamping regions 11, 117, it is then possible, as described above, to introduce an adhesive material into the regions 15, 17, 19 or 119 concerned and into the annular space between the fluid capillary 105 and the inner walling of the aperture in the supporting element 109.

As already indicated above, the supporting element 109 may also be fixed in the region 121 by the method explained above.

If a thermoplastic material that displays a swelling behavior when heated above a minimum temperature is chosen as the material for the main body, this may counteract the desired shrinkage process when cooling down, with the result that in an extreme case sufficient fixing between the insert and the main body in the clamping regions 11, 117 is no longer obtained. This problem can be averted by such a material not being heated beyond a certain maximum temperature, from which a disadvantageous swelling behavior such as this is displayed to an inadmissible degree.

Materials that display such a swelling behavior are, for example, thermoplastic materials from the group of polyether ketones, in particular PEEK, PEKEK etc.

However, such a swelling process can be reversed if the main body is heated over a sufficient time to a temperature within a conditioning range. The conditioning range in this case lies below the melting temperature for the crystalline phase of the material. Such conditioning achieves the effect that a certain maximum fraction of the amorphous phase of the material changes again into a crystalline phase, which has a smaller volume than the amorphous phase. Sufficient holding forces are thereby obtained again.

This material property may be used separately or in conjunction with the procedure described above for the assembly of the inserts, in order to achieve sufficient fixing of the inserts in the main body.

For example, a main body with a starting material that only has a relatively small fraction of the crystalline phase may be used. The swelling behavior when it undergoes heating is accordingly minor. In addition, conditioning for a certain time can achieve the effect that greater pressing forces between the main body and the insert are obtained than in the case of just cooling, since an additional shrinking behavior of the material is produced here.

In an extreme case, the aperture may also be prefabricated in the region of the clamping regions 11, 117 in such a way that it already has greater cross-sectional dimensions than the inserts in the initial state. Assembly can then take place in such a way that the insert concerned is inserted into the clamping region, 11, 117 (and possibly also 121) and positioned. This is followed by conditioning for a sufficiently long time period, whereby a shrinkage process is obtained in the way explained above. It goes without saying that it is also necessary for this to use in the initial state a material with a relatively small crystalline phase. This presupposes that close tolerances are maintained in the prefabrication, in order to produce sufficiently great radial clamping forces after the shrinkage process.

It goes without saying that, as described above, the adhesive material may subsequently be introduced as protection or for the additional fixing of the insert.

In the phase of the increase in volume of the main body, whether just due to the thermal expansion or due to the additional swelling process, a shaping may also take place on an outer surface of the main body. For this purpose, the expansion can be suppressed in a predetermined partial region by means of a molding element. For example, in the case of the coupling element 100 in FIG. 2, before the beginning of an increase in the temperature of the main body 103, a molding element in the form of a ring with a predetermined inner diameter is placed around the positioning region 125. Instead of the use of a ring or a molding element, it goes without saying that the main body may also be placed into a corresponding device which, in addition to the molding, serves for the heating of the main body.

The molding element consequently restricts the expansion as a result of the thermal expansion and/or as a result of the swelling process. This leads to a plastic deformation of the material in this region. The molding element may in this case have an inner walling with a predetermined structure, with the result that, presupposing a sufficient expansion or increase in volume, the circumferential surface 125*a* of the positioning region 125 can be provided with a corresponding structure. It goes without saying that, instead of this, merely an improved smoothness of the circumferential surface 125*a* of the cylindrical positioning region 125 or a cross section that is as exactly circular as possible (or else of course any predetermined cross section desired) can also be achieved.

It goes without saying that the reduction in volume that occurs when cooling down to a temperature within the working range must be taken into consideration in the dimensioning of the molding element.

The same may also take place in the production of an inner surface, for example the inner walling 13*a* of the recess 13 in the end face of the main body 3 in the case of the optical plug shown in FIG. 1.

It goes without saying that the shaping of an inner surface must take place in this case during the shrinkage or the reduction in volume of the material, irrespective of whether this is caused by cooling or a shrinkage process as a result of the transformation of the amorphous fraction into a crystalline fraction of the material of the main body. For this, a molding element may be inserted into the recess 13 before the shrinkage process or the decrease in volume of the material of the main body 3 begins. If the molding element is dimensioned in such a way that the shrinkage process in the region of the recess 13 or the inner walling 13*a* is restricted, there is in turn a plastic shaping of the material in this region. An improvement of the smoothness of the inner walling can in turn be achieved, or the production of a desired structure, such as a cross section that is as exactly circular as possible.

It goes without saying that in both cases the shaping may also be used for achieving a dimensioning (of the cross section) that is as exact as possible after the cooling.

It is likewise possible to use a material that displays this swelling behavior only for the insert 7, 105, 109 or both for the insert 7, 105, 109 and for the main body 3, 103. The thermal process must then be devised in such a way that, after its completion, sufficiently great clamping forces are obtained. This may take place by a swelling of the material of the insert 7, 105, 109 or by a reduction in the volume of the material of the main body 3, 103 in the way described above.

In all of the variants, the production method explained above allows excellent and easy fixing of an insert in a main body, the connection having excellent stableness and/or fluidic tightness without any melting of the material or the use of an adhesive. In this way, even low-dispersion connections are possible without the use of further components, such as ferrules, seals, etc., just by the use of a thermal expansion or contraction or shrinkage process.

LIST OF REFERENCE SIGNS

1 Connection component/optical plug
3 Main body

3a End face
5 Aperture
7 Optical waveguide
7a Coating
11 Clamping region
13 Recess
13a Inner walling
15 Region
17 Region
19 Region
100 Connection component/coupling element
103 Main body
105 Fluid capillary
105a Coating
107 Aperture
109 Supporting element
111 Widened region
113 Recess
115 Seal
117 Clamping region
119 Region
121 Region
123 Middle region
125 Positioning region
125a Circumferential surface

What is claimed is:

1. A method for producing a fluidic connection component for chromatography, the fluidic component comprising a main body and at least one optical waveguide held in the main body, wherein the main body is prefabricated with at least one aperture for the at least one optical waveguide, the method comprising:
   connecting the at least one optical waveguide to the main body securely and fluidically tightly by purely a thermal expansion of the main body or the optical waveguide, in which the thermal expansion only occurs during a thermal process, wherein there is no initial or full melting of a contact region between the main body and the at least one optical waveguide, and
   after completion of the thermal process, retaining a thermally induced change in volume of the main body or of the optical waveguide to cause a radial clamping force between the main body and the optical waveguide to occur in a clamping region along a course of the aperture to form a secure and fluidically tight connection between the main body and the optical waveguide at temperatures within a working temperature range,
   wherein a material with a first coefficient of thermal expansion is used for the main body and a material with a second coefficient of thermal expansion is used for the at least one optical waveguide, the first coefficient of thermal expansion is at least twice the second coefficient of thermal expansion, or a material with a third coefficient of thermal expansion is used for the at least one optical waveguide and a material with a fourth coefficient of thermal expansion is used for the main body, the third coefficient of thermal expansion is at least twice the fourth coefficient of thermal expansion.

2. The method of claim 1, wherein the material with the first coefficient is a plastic and the material with the second coefficient is selected from the group consisting of a glass, a ceramic, a metal, and a metal alloy, or wherein the material with the third coefficient is selected from the group consisting of a glass, a ceramic, a metal, and a metal alloy and the material with the fourth coefficient is a plastic.

3. The method of claim 1, wherein
   a) an inner dimension of the aperture of the main body at a temperature within the working temperature range is smaller than a dimension of a cross section of the optical waveguide at a temperature within the working temperature range,
   b) the method further comprising: adjusting a temperature of the main body and the optical waveguide to a predetermined common temperature outside of the working temperature range or a predetermined temperature difference between the material of the main body and the material of the optical waveguide,
   c) inserting the optical waveguide into the aperture, and
   d) securely holding the optical waveguide fluidically tightly in the main body when a temperature of the optical waveguide and the main body are within the working temperature range.

4. The method of claim 1, wherein
   a) the material used for the main body or for the at least one optical waveguide is
      i) partially of a crystalline phase and partially of an amorphous phase,
      ii) in which, when heated above a melting temperature for the crystalline phase, and the melting temperature is above the working temperature range, displays an increase in volume as a result of a conversion of part of the crystalline phase into the amorphous phase, and with a cooling does not have a complete restoration of the fraction of the crystalline phase that has been transformed into the amorphous phase back into the crystalline phrase, and
      iii) in which, at a temperature within a conditioning range, in which the conditioning range is below the melting temperature of the crystalline phase and above the working temperature range, displays a decrease in volume as a result of a transformation of the amorphous of the amorphous phase into the crystalline phase, until a minimum volume is reached on reaching a maximum fraction of the crystalline phase, and
   b) the method further comprising selecting a material and a fraction of the crystalline phase in the material of the prefabricated main body or the at least one optical waveguide and a temperature profile of the thermal process, where a secure fluidically tight connection between the at least one optical waveguide and the main body is obtained after the thermal process.

5. The method of claim 4, wherein
   a) an inner dimension of the aperture of the main body at a temperature within the working temperature range is greater than a dimension of a cross section of the optical waveguide at a temperature within the working temperature range,
   b) the method further comprising: inserting the optical waveguide into the aperture,
   c) heating the main body to a temperature within the conditioning range where the optical waveguide is held securely and fluidically tightly in the main body either at the temperature within the conditioning range or after cooling to a temperature within the working temperature range.

6. The method of claim 4, wherein an expansion of an outer dimension of the main body during the thermal process on at least one outer surface of the main body is restricted by a molding element to cause a plastic deformation of the main body in a region of the at least one outer surface.

7. The method of claim 6, wherein a structure of the outer surface is determined by the molding element.

8. The method of claim 6, wherein the at least one outer surface is a closed annular surface.

9. The method of claim 6, wherein an expansion of the outer dimension of the main body is in a region radially surrounding the clamping region and an additional increase in the radial clamping forces is produced in a region of the clamping region by the plastic deformation.

10. The method of claim 6 wherein, during the cooling or conditioning of the main body, a shrinkage process on at least one inner surface of the main body is restricted by the molding element to cause the plastic deformation of the main body to a defined form in a region of the at least one inner surface.

11. The method of claim 10, wherein a structure of the inner surface of the main body is determined by the molding element.

12. The method of claim 11, wherein the at least one inner surface is a closed annular surface.

13. The method of claim 1, wherein the at least one optical waveguide has a coating, which is removed in a front region, in which the optical waveguide is connected to the main body by a thermal expansion and a shrinkage process.

14. The method of claim 13, wherein a rearward partial region of the optical waveguide, in which the coating has been removed and which lies on a side of the clamping region that is facing away from the front end of the optical waveguide, is protected, and connected to the main body with an adhesive material.

15. The method of claim 1, wherein the main body is prefabricated with at least two apertures, and the optical waveguide is inserted in one of said apertures and a fluid capillary is inserted in another of said apertures and are connected to the main body securely and fluidically tightly by a single thermal process.

16. The method of claim 1 further comprising: coupling the optical waveguide to a chromatography column.

17. The method of claim 1 further comprising: coupling the optical waveguide to a sensor.

18. A method for producing a fluidic connection component for chromatography, the fluidic connection component comprising a main body and a fluid capillary held in the main body, wherein the main body is prefabricated with at least one aperture for the fluid capillary, the method comprising:
  connecting the fluid capillary to the main body securely and fluidically tightly by purely a thermal expansion of the main body or the fluid capillary, in which the thermal expansion occurs during a thermal process, wherein there is no initial or full melting of a contact region between the main body and the fluid capillary, and
  after completion of the thermal process, retaining a thermally induced change in volume of the main body or of the fluid capillary to cause a radial clamping force between the main body and the fluid capillary to occur in a clamping region along a course of the aperture to form a secure and fluidically tight connection between the main body and the fluid capillary at temperatures within a working temperature range,
  wherein a material with a first coefficient of thermal expansion is used for the main body and a material with a second coefficient of thermal expansion is used for the fluid capillary, the first coefficient of thermal expansion is at least twice the second coefficient of thermal expansion, or a material with a third coefficient of thermal expansion is used for the fluid capillary and a material with a fourth coefficient of thermal expansion is used for the main body, the third coefficient of thermal expansion is at least twice the fourth coefficient of thermal expansion.

19. The method of claim 18, wherein the main body is prefabricated with at least two apertures, and the fluid capillary is inserted in one of said apertures and an optical waveguide is inserted in another of said apertures and are connected to the main body securely and fluidically tightly by a single thermal process.

* * * * *

UNITED STATES PATENT AND TRADEMARK OFFICE
CERTIFICATE OF CORRECTION

PATENT NO. : 9,956,651 B2
APPLICATION NO. : 14/200392
DATED : May 1, 2018
INVENTOR(S) : Erik Balgar et al.

Page 1 of 1

It is certified that error appears in the above-identified patent and that said Letters Patent is hereby corrected as shown below:

In the Claims

Claim 4, Column 16, Line 32: delete "phrase" and insert --phase--

Claim 4, Column 16, Line 38: after "amorphous" delete "of the amorphous"

Signed and Sealed this
Seventeenth Day of March, 2020

Andrei Iancu
*Director of the United States Patent and Trademark Office*